(12) United States Patent   (10) Patent No.: US 8,968,386 B2
Svensson                          (45) Date of Patent:    Mar. 3, 2015

(54) STENT AND METHOD FOR MAINTAINING THE AREA OF A BODY LUMEN

(71) Applicant: The Cleveland Clinic Foundation, Cleveland, OH (US)

(72) Inventor: Lars G. Svensson, Gates Mills, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/939,476

(22) Filed: Jul. 11, 2013

(65) Prior Publication Data

US 2014/0018904 A1    Jan. 16, 2014

Related U.S. Application Data

(60) Provisional application No. 61/670,269, filed on Jul. 11, 2012.

(51) Int. Cl.
| | |
|---|---|
| *A61F 2/06* | (2013.01) |
| *A61F 2/89* | (2013.01) |
| *A61F 2/915* | (2013.01) |
| A61F 2/24 | (2006.01) |

(52) U.S. Cl.
CPC . *A61F 2/89* (2013.01); *A61F 2/915* (2013.01);
*A61F 2/2412* (2013.01); *A61F 2/2418* (2013.01); *A61F 2250/0018* (2013.01); *A61F 2220/0016* (2013.01); *A61F 2230/0054* (2013.01)
USPC ........................................ 623/1.16; 623/1.32

(58) Field of Classification Search
CPC ....................................................... A61F 2/94
USPC .............................................. 623/1.16, 1.32
See application file for complete search history.

(56) References Cited

U.S. PATENT DOCUMENTS

| | | | |
|---|---|---|---|
| 5,449,373 A | 9/1995 | Pinchasik et al. | |
| 6,270,524 B1 | 8/2001 | Kim | |
| 7,794,492 B2 | 9/2010 | Ishimaru et al. | |
| 7,862,608 B2 * | 1/2011 | Hogendijk et al. | 623/1.22 |
| 2001/0041930 A1 * | 11/2001 | Globerman et al. | 623/1.16 |
| 2007/0173921 A1 * | 7/2007 | Wholey et al. | 623/1.13 |

* cited by examiner

*Primary Examiner* — Bruce E Snow
*Assistant Examiner* — Brian Dukert
(74) *Attorney, Agent, or Firm* — Tarolli, Sundheim, Covell & Tummino LLP

(57) ABSTRACT

A stent comprises (a) a first segment that is radially compressible and expandable and (b) a second segment that is substantially rigid in a radial direction. The second segment is bendable to assume a curved configuration while remaining substantially rigid in the radial direction and thereby resisting radial compression and expansion.

7 Claims, 3 Drawing Sheets

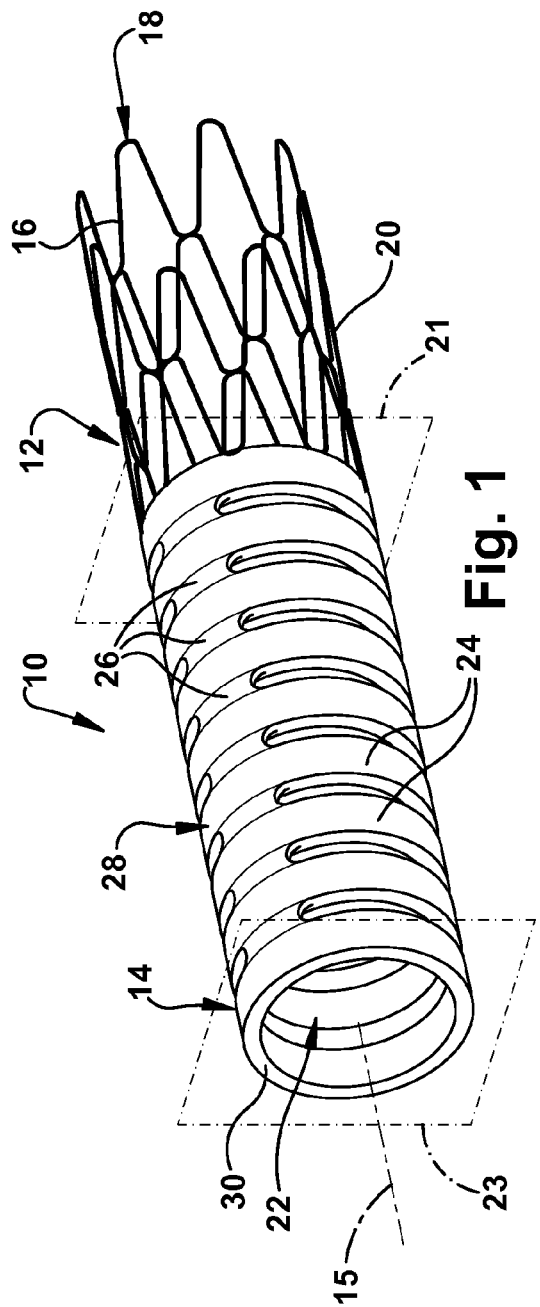
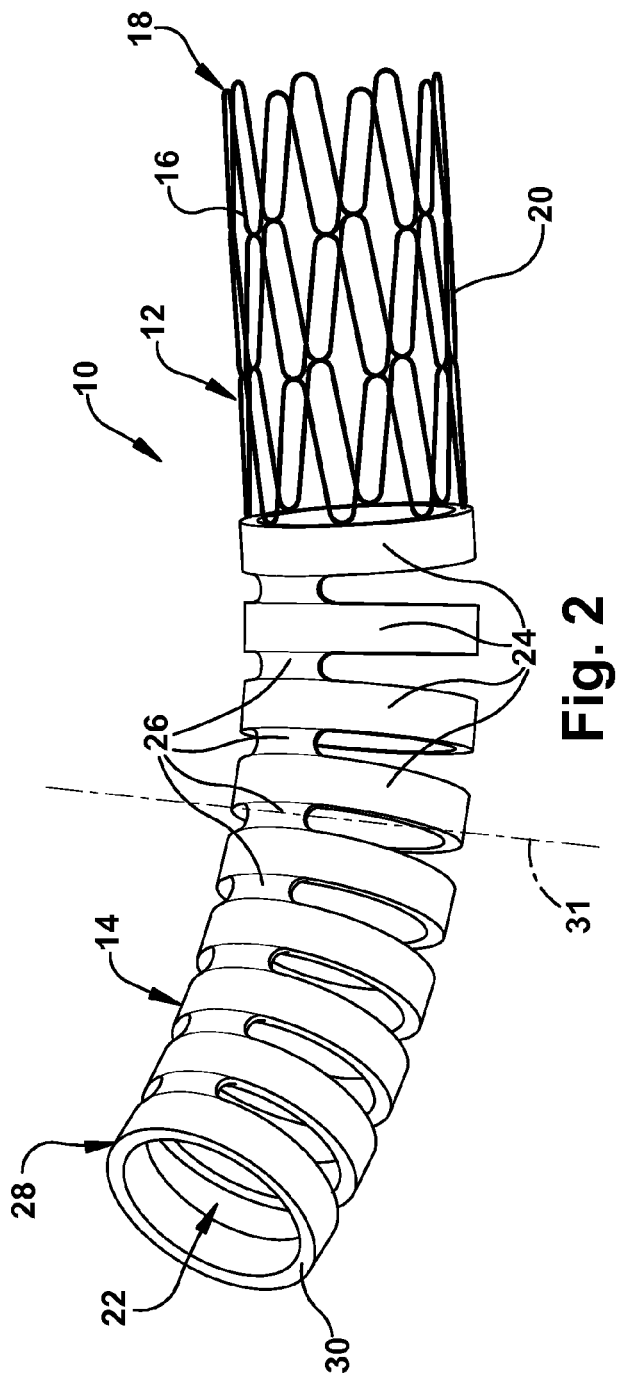

STENT AND METHOD FOR MAINTAINING THE AREA OF A BODY LUMEN

RELATED APPLICATION

This application claims the benefit of U.S. Provisional Appln. No. 61/670,269, filed Jul. 11, 2012, the subject matter of which is incorporated herein in its entirety.

FIELD OF THE INVENTION

The present invention relates to a stent and to a method for helping to maintain the cross-sectional area of a body lumen and, more particularly, to a stent that has a radially compressible and expandable segment and a segment that resists radial compression and expansion and to a method for helping to maintain the cross-sectional area of a body lumen with such a stent.

BACKGROUND OF THE INVENTION

Aortic valve replacement is a medical procedure commonly used to address medical problems associated with a regurgitant or stenotic aortic heart valve. Replacement valves may be made of animal tissue or other materials and may be implanted via open heart surgery or, in some cases, via a catheter. Whether a replacement valve is made of animal tissue or another material, there may be a need to help prevent adjacent blood vessels, such as coronary arteries, from being compressed or otherwise obstructed by the replacement valve.

SUMMARY OF THE INVENTION

The present invention is directed to a stent and to a method for helping to maintain the cross-sectional area of a body lumen and, more particularly, to a stent that has a radially compressible and expandable segment and a segment that resists radial compression and expansion and to a method for helping to maintain the cross-sectional area of a body lumen with such a stent.

In a representative embodiment of the present invention, a stent comprises (a) a first segment that is radially compressible and expandable and (b) a second segment that is substantially rigid in a radial direction. The second segment is bendable to assume a curved configuration while remaining substantially rigid in the radial direction and thereby resisting radial compression and expansion.

In accordance with another example of the invention, a method for helping to maintain the cross-sectional area of a body lumen uses a stent. The stent includes a first segment that is radially compressible and expandable and a second segment that is substantially rigid in a radial direction. The second segment is bendable to assume a curved configuration while remaining substantially rigid in the radial direction and thereby resisting radial compression and expansion. The method comprises the steps of positioning the first segment of the stent in a first body lumen and positioning the second segment of the stent in a second body lumen. The method also comprises the step of expanding the first segment of the stent in the first body lumen so as to engage a wall defining the first body lumen and thereby to anchor the stent in the first body lumen. The method further comprises the step of bending the second segment of the stent so that the second segment of the stent extends at least partially in a lengthwise direction of the second body lumen.

BRIEF DESCRIPTION OF THE DRAWINGS

The foregoing and other features and advantages of the present invention will become apparent to those skilled in the art to which the present invention relates upon reading the following description with reference to the accompanying drawings, in which:

FIG. 1 is a perspective view of an embodiment of a stent in accordance with the present invention in an undeployed condition;

FIG. 2 is a perspective view of the stent of FIG. 1 in a partially deployed condition;

DESCRIPTION OF EMBODIMENTS

Figure 3:
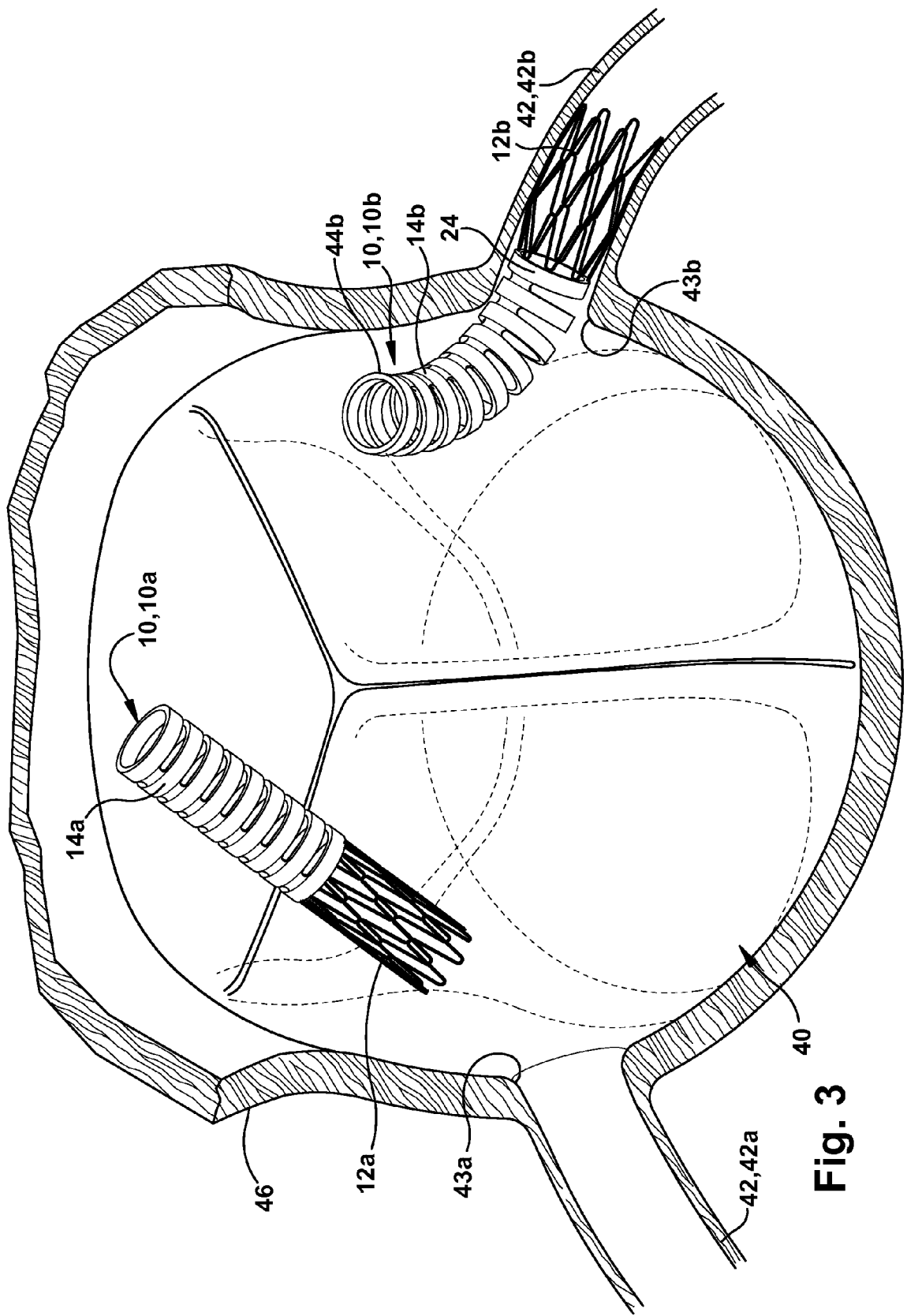
FIG. 3 is a perspective view of two stents as shown in FIG. 1 in different stages of implantation in coronary arteries.

FIGS. 1 and 2 depict a stent 10 in accordance with an example of the present invention. The stent 10 comprises first and second segments 12 and 14 arranged end-to-end in series. In other words, the first and second segments 12 and 14 are arranged sequentially along the length of the stent 10. The length of the stent 10 is a dimension along a central longitudinal axis 15 of the stent.

The first segment 12 includes a wire 16 bent or otherwise formed in a zigzag configuration. The wire 16 may be fabricated from any suitable biocompatible material, such as medical grade stainless steel, titanium, or nitinol. The zigzag-shaped wire 16 is formed into a tube 18 with the wire defining the wall 20 of the tube and the zigzags extending circumferentially around the wall. The tube 18 and the wall 20 are substantially circular in radial cross-section, as viewed in a plane, such as plane 21, that is substantially perpendicular to the central longitudinal axis 15. The wall 20 of the tube 18 partially defines a lumen 22 extending lengthwise through the stent 10 along the central longitudinal axis 15. Because the wire 16 has a zigzag configuration, the tube 18 of the first segment 12 of the stent 10 can be expanded radially from the undeployed condition shown in FIG. 1. When the tube 18 is expanded, an outer diameter and an outer circumference of the tube 18 are increased as compared to the original undeployed condition of the tube.

The second segment 14 of the stent 10 includes a series of metal rings 24. The rings 24 may be fabricated from any suitable biocompatible material, such as medical grade stainless steel, titanium, or nitinol. The rings 24 are, in effect, short tubes disposed coaxially with respect to each other. Each ring 24 is separated or spaced axially a short distance from the adjacent ring or rings. All of the rings 24 are joined together by a row of connecting portions or interconnecting strips 26 to form a longer tube 28. Each of the interconnecting strips 26 extends only a relatively short distance along the central longitudinal axis 15 and only a relatively short distance around the circumference of the tube 28. In other words, each of the interconnecting strips 26 extends substantially less than completely around the circumference of the tube 28 and second segment 14. More particularly, the interconnecting strips 26 extend around less than one-half of the circumference of the tube 28, and may extend around, for example, less than one-quarter of the circumference. The interconnecting strips 26, like the rings 24, may be fabricated from any suitable biocompatible material, such as medical grade stainless steel, titanium, or nitinol. Although the connecting portions or interconnecting strips 26 are shown as narrow bands or strips, they may have other configurations that will facilitate bending of the tube 28 and the second segment 14, as is described below.

Just as the zigzag shaped wire 16 defines the wall 20 of the tube 18 of the first segment 12, the rings 24 and the interconnecting strips 26 define the wall 30 of the tube 28. Like the tube 18 and the wall 20 of the first segment 12, the tube 28 and the wall 30 are substantially circular in radial cross-section, as viewed in a plane, such as the plane 23, that is substantially perpendicular to the central longitudinal axis 15. The plane 23 is parallel to the plane 21 when the stent 10 is in its undeployed condition shown in FIG. 1. Also, like the wall 20 of the tube 18, the wall 30 of the tube 28 partially defines the lumen 22 extending lengthwise through the stent 10 along the central longitudinal axis 15. Unlike the wire 16 and the tube 18 of the first segment 12, however, the rings 24 and the tube 28 of the second segment 14 cannot be expanded radially from the condition shown in FIG. 1. The tube 28 of the second segment 14 of the stent 10 is thus substantially rigid in a radial direction, as viewed in a plane, such as the plane 23, that is substantially perpendicular to the central longitudinal axis 15. The outer diameter and outer circumference of the tube 28 cannot be increased and are substantially fixed.

Due to the axial separation or spacing between adjacent rings 24 and the relatively small circumferential extent of the interconnecting strips 26, the tube 28 of the second segment 14 can be bent or deflected. The arrangement of rings 24 and interconnecting strips 26 permits deflection of the tube 28 as though, for example, the rings 24 were ribs and the row of interconnecting strips were a spinal column joining the ribs. FIG. 2 shows the row of interconnecting strips 26 after having been bent so that the tube 28 of the second segment 14 of the stent 10 is deflected or curved about an axis 31 disposed outside of the tube and adjacent to the interconnecting strips. Such deflection or curvature is possible even though the tube 28 of the second segment 14 of the stent 10 is and remains substantially rigid in a radial direction.

The first and second segments 12 and 14 of the stent 10 are joined end-to-end with one of the rings 24 being welded or otherwise fixed or immovably joined to the wire 16. The tube 18 of the first segment 12 can be expanded radially from the undeployed condition shown in FIG. 1, except at the end of the tube 18 that is fixed to the second segment 14. The tube 18 of the first segment can also be compressed into the condition shown in FIG. 1. The tube 28, on the other hand, resists radial expansion and compression and is substantially rigid in the radial direction.

The difference between the radial expansion characteristics of the first and second segments 12 and 14 of the stent 10 facilitates use of the stent to inhibit obstruction of a lumen in the human body. By way of example, FIG. 3 illustrates two stents 10 in different stages of installation adjacent the aortic valve 40 of a human heart. The stent 10 on the left-hand side of FIG. 3 is identified hereafter as the left stent 10a, and the stent on the right-hand side of FIG. 3 is identified hereafter as the right stent 10b.

The left stent 10a, as viewed in FIG. 3, is positioned in the aorta 46 and above the aortic valve 40 for implantation in a coronary artery 42 on the left-hand side of FIG. 3. The coronary artery 42 on the left-hand side of FIG. 3 is identified hereafter as the left coronary artery 42a. Similarly, the right stent 10b, as viewed in FIG. 3, is positioned in the aorta 46 and above the aortic valve 40 and is partially implanted in a coronary artery 42 on the right-hand side of FIG. 3. The coronary artery 42 on the right-hand side of FIG. 3 is identified hereafter as the right coronary artery 42b.

The first segment 12a of the left stent 10a is positioned closer to the left coronary artery 42a than the second segment 14a of the left stent. The first segment 12a of the left stent 10a is oriented so that the first segment can be inserted in its undeployed condition into the left coronary artery 42a. The illustrated positioning of the left stent 10a in FIG. 3 represents a first step in the implantation of a stent 10 adjacent the aortic valve 40. A second step in the implantation of a stent 10 adjacent the aortic valve 40 is represented by the positioning of the right stent 10b in FIG. 3. The first segment 12b of the right stent 10b has been fully inserted into the right coronary artery 42b. At least one ring 24 of the second segment 14b of the right stent 10b, such as the ring closest to the first segment 12b of the right stent, is positioned in the ostium 43b of the right coronary artery 42b. Having a ring 24 positioned in the ostium 43b helps to maintain the cross-sectional flow area of the ostium and the right coronary artery 42b. A majority of the second segment 14b of the right stent 10b remains positioned in the aorta 46, however.

A third step in the implantation of a stent 10 adjacent the aortic valve 40 is to expand the first segment 12 of the stent to engage the wall of the coronary artery 42. More specifically, with reference to the right stent 10b, which is illustrated with its first segment 12b in the right coronary artery 42b, the first segment 12b is expanded to engage the interior surface of the wall of the right coronary artery. Expansion of the first segment 12b helps to anchor the right stent 10b in the right coronary artery 42b and thereby helps to keep the second segment 14b of the right stent properly positioned relative to the aortic valve 40. Anchoring of the right stent 10b may be achieved solely as a result of outward pressure of the expanded first segment 12b of the right stent on the wall of the right coronary artery 42b. Alternatively, such anchoring may be supplemented by providing small hooks or barbs (not shown) on the first segment 12b of the right stent 10b.

A fourth step in the implantation of a stent 10 adjacent the aortic valve 40 is represented by the relative alignment of the first and second segments 12b and 14b of the right stent 10b in FIG. 3. Specifically, the second segment 14b of the right stent 10b has been bent so that the end portion 44b of the second segment farthest from first segment 12b is generally in lengthwise alignment with the aorta 46 and extends generally parallel to the portion of the aorta in which the end portion 44b is located. As a result, the first segment 12b of the right stent 10b extends in the lengthwise direction of the right coronary artery 42b and the lumen defined by the right coronary artery. At the same time, at least the end portion 44b of the second segment 14b of the right stent 10b extends in the lengthwise direction of the aorta 46 and the lumen defined by the aorta.

Although the foregoing description relates to expansion and anchoring of the first segment 12b of the right stent 10b and bending of the right stent, the first segment 12a of the left stent 10a would similarly be positioned in the left coronary artery 42a and expanded to engage the interior surface of the wall of the left coronary artery and anchor the left stent in position. Likewise, the left stent 10a would be bent in the same general way as the right stent 10b so that the first segment 12a of the left stent extends in the lengthwise direction of the left coronary artery 42a and the lumen defined by the left coronary artery, and at least an end portion of the second segment 14a of the left stent farthest from first segment 12a extends in the lengthwise direction of the aorta 46 and the lumen defined by the aorta.

Figure 4:
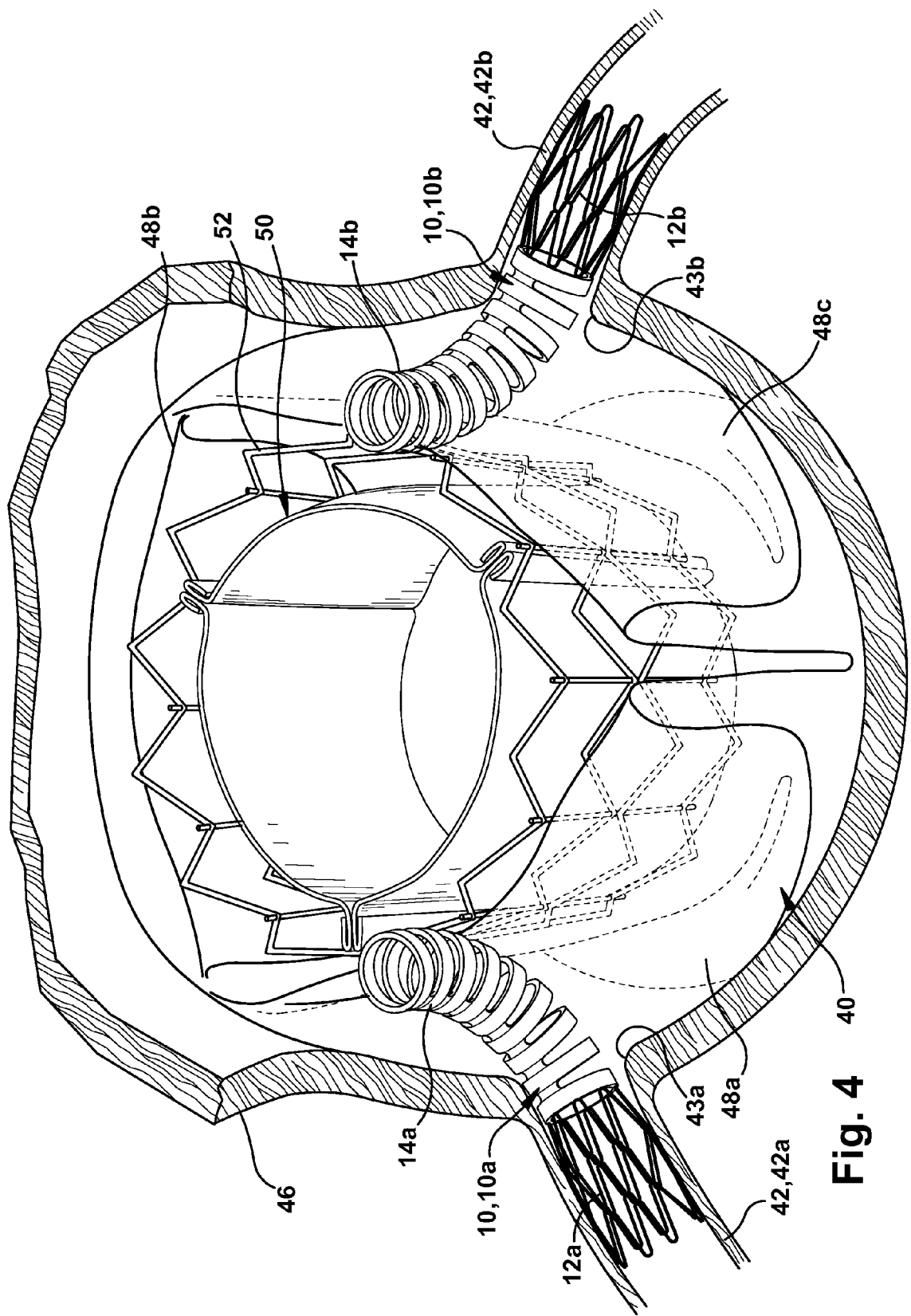
FIG. 4 is a perspective view of the stents of FIG. 3 when fully implanted in the coronary arteries.

FIG. 4 illustrates how the left and right stents 10a and 10b of FIG. 3 help to inhibit obstruction of the left and right coronary arteries 42a and 42b when an artificial valve 50 is implanted to help, for example, correct a regurgitant aortic valve 40. In FIG. 4, the left and right stents 10*a* and 10*b* have been implanted in the left and right coronary arteries 42*a* and 42*b*, respectively, as described above with reference to FIG. 3. The artificial valve 50 has then been implanted within the three leaflets 48*a*, 48*b*, and 48*c* of the aortic valve 40. To hold the leaflets 48*a*-48*c* of the aortic valve 40 in a non-functioning position so that the artificial valve 50 can function in place of the aortic valve 40, a stent 52 has been implanted within the three leaflets and expanded to hold the leaflets and the aortic valve in an "open" position. The artificial valve 50 has been positioned inside the stent 52 and functions to move between an open condition (shown) and a closed position (not shown) to permit blood flow into the aorta 46 and inhibit reverse flow out of the aorta, respectively.

As shown in FIG. 4, the stent 52 implanted in the aortic valve 40 holds the leaflets 48*a*-*c* of the aortic valve in an upright, "open" position close to the wall of the aorta 46. It is possible that, without the left and right stents 10*a* and 10*b*, the leaflets 48*a*-*c* might be positioned so close to the ostia 43*a* and 43*b* of the left and right coronary arteries 42*a* and 42*b*, respectively, that one or both of the left and right coronary arteries would be wholly or partially obstructed or occluded. It is also possible that although the leaflets 48*a*-*c* might be spaced appropriately away from the ostia 43*a* and 43*b* of the left and right coronary arteries 42*a* and 42*b*, the radial expansion of the stent 52 to hold the leaflets in an open position may compress the tissue adjacent the ostia, thereby wholly or partially obstructing or occluding one or both of the left and right coronary arteries. Further, it is possible that the spacing between the leaflets 48*a*-*c* of the aortic valve 40 and the left and right coronary arteries 42*a* and 42*b* may facilitate the deposit of plaques adjacent the ostia 43*a* and 43*b* of one or both of the left and right coronary arteries, thereby wholly or partially obstructing or occluding the left and right coronary arteries over time. Installation of the left and right stents 10*a* and 10*b* helps to inhibit obstruction or occlusion of the left and right coronary arteries 42*a* and 42*b* from each of the foregoing causes and thus helps to maintain the cross-sectional flow area of the left and right coronary arteries.

More particularly, the left and right stents 10*a* and 10*b* are implanted in the left and right coronary arteries 42*a* and 42*b*, respectively, so that the second segments 14*a* and 14*b* of the two stents maintain a minimum spacing between the leaflets 48*a*-*c* and the ostia 43*a* and 43*b* of the coronary arteries. The second segments 14*a* and 14*b* of the left and right stents 10*a* and 10*b* are interposed both between the leaflets 48*a*-*c* and the wall of the aorta 46 and between the leaflets and the ostia 43*a* and 43*b* of the left and right coronary arteries 42*a* and 42*b*, respectively. Because the rings 24 of the second segments 14*a* and 14*b* are substantially rigid in a radial direction and thereby resist radial compression and expansion, the second segments of the left and right stents 10*a* and 10*b* maintain a minimum spacing between the leaflets 48*a*-*c* and both the wall of the aorta 46 and the ostia 43*a* and 43*b* of the left and right coronary arteries 42*a* and 42*b*.

In use, the stent 10 may be implanted in a blood vessel, such as a coronary artery 42, in a patient's body during a surgical procedure in which the patient's body cavity is opened to facilitate the procedure, such as during open heart surgery. With such an "open" surgical procedure, the stent 10 may be implanted by a surgeon via direct manual manipulation. Alternatively, it may be possible to implant the stent 10 using a balloon catheter (not shown) introduced into a patient's body through a blood vessel.

Although the first segment 12 of the stent 10 of FIGS. 1-2 is described and illustrated as including and being constructed of a wire 16 bent or otherwise formed in a zigzag configuration, the first segment may be constructed in other ways so that the first segment has a tubular shape and is radially compressible and expandable. The first segment 12 may, for example, be formed by bending wire, by weaving wire, or by machining, laser cutting, or chemical etching a tube that initially has a solid wall or walls. The configuration of the wire 16, which is shown as a zigzag in FIGS. 1 and 2 may be any other suitable configuration, such as a spiral or an array of diamonds or a combination of configurations. Such configurations may also be achieved by, for example, machining, laser cutting, or chemical etching a tube that initially has a solid wall or walls.

The first and second segments 12 and 14 of the stent 10 may be circular in radial cross-section, as shown in FIGS. 1 and 2, or may have any other suitable shapes in radial section, such as oval, hexagonal, octagonal, square, or rectangular. The first and second segments 12 and 14 may also have shapes that are different in radial section from each other. While the second segment 14 of the stent 10 is shown in FIG. 2 as being bent or deflected into a curved or arcuate configuration about an axis 31 having a particular orientation with respect to the second segment and the central longitudinal axis 15 of the stent, the second segment may be bent or deflected about an axis having a different relative orientation with respect to the second segment and the central longitudinal axis. The second segment 14 may also be bent or deflected about a plurality of axes having different orientations as may be required for the second segment to be positioned appropriately to inhibit obstruction or occlusion of a lumen in which the first segment 12 is positioned.

As shown in FIGS. 1-2, the stent 10 has a single radially compressible and expandable first segment 12. The stent 10 may, however, have more than one such radially compressible and expandable first segment, if desired. For example, the stent 10 might have two such first segments 12 separated by a second segment 14 that resists radial compression and expansion. Similarly, while the stent 10 of FIGS. 1-2 has a single second segment 14 that is substantially rigid in a radial direction, thereby resisting radial compression and expansion, the stent may have more than one such second segment, if desired. For example, the stent 10 might have two such second segments 14 separated by a radially compressible and expandable first segment 12. Larger numbers of first and second segments 12 and 14 may also be included in the stent 10.

Although the stent 10 is shown in FIGS. 3 and 4 being implanted in the coronary arteries 42 adjacent the aorta 46 of a patient, the stent may be implanted in other blood vessels, such the carotid arteries and the subclavian arteries. The stent 10 may also be used in other organs of the body, such as a kidney, or in a lumen of any organ of the body, such as a ureter. Further, while use of the stent 10 has been described in connection with a method for inhibiting obstruction of a blood vessel or other body lumen, the stent could also be used to inhibit collapse of a blood vessel or other body lumen. Such a collapse may occur, for example, in a branch artery after a stent is implanted in a patient's aorta. More generally, therefore, the stent 10 is used to help maintain the cross-sectional area or the flow area of a body lumen.

As previously described, the stent 10 of FIGS. 1-2 is fabricated of a material that is inherently radiopaque. The stent 10 may alternatively be fabricated of a material that is not inherently radiopaque. In the latter case, a radiopaque coating may be applied to some portion of the stent 10 or such portion of the stent may be caused to be radiopaque through another mechanism to facilitate placement of the stent via a catheter or other remote placement mechanism. The stent 10 of FIGS. 1-2 or one of the first and second segments 12 and 14 of the stent may be coated with a pharmaceutical or other therapeutic agent, which may be released, leached, diffused, or otherwise provided to a target tissue.

From the above description of the invention, those skilled in the art will perceive improvements, changes and modifications. Such improvements, changes and modifications within the skill of the art are intended to be covered by the appended claims.

Having described the invention, the following is claimed:

1. A method for helping to maintain the cross-sectional area of a body lumen using a stent, the stent including at least a first end segment that is radially compressible and expandable and at least a second end segment being bendable to assume a curved configuration while resisting radial compression and expansion in a deployed state, said method comprising:
    (a) positioning the at least first end segment of the stent in a coronary ostia;
    (b) positioning the at least second end segment of the stent in an aorta;
    (c) expanding the at least first end segment of the stent in the coronary ostia so as to engage a wall defining the coronary ostia and thereby to anchor the stent in the coronary ostia; and
    (d) bending the at least second end segment of the stent without increasing the outer diameter of the at least second end segment so that the at least second end segment of the stent extends at least partially in a lengthwise direction of the aorta.

2. The method of claim 1 wherein the first and second segments of the stent are arranged sequentially relative to each other along the stent.

3. The method of claim 1, wherein the step of positioning the second segment of the stent in the aorta includes positioning the second segment of the stent to inhibit obstruction of the coronary ostia by a replacement valve.

4. The method of claim 1 wherein each of the first and second segments of the stent has a tubular shape.

5. The method of claim 1 wherein the second segment of the stent includes a plurality of rings that are substantially rigid in the radial direction, the rings being coaxial prior to bending of the second segment.

6. The method of claim 5 wherein the rings are spaced apart axially from each other.

7. The method of claim 6 wherein adjacent rings are joined together by connecting portions that extend less than completely around a circumference of the second segment.

\* \* \* \* \*